United States Patent
Noll et al.

(10) Patent No.: US 8,536,397 B2
(45) Date of Patent: Sep. 17, 2013

(54) RECOVERY OF BENZENE AND BENZENE DERIVATIVES FROM GASOLINE FRACTION AND REFINERY STREAMS

(75) Inventors: Oliver Noll, Castrop-Rauxel (DE); Helmut Gehrke, Bergkamen (DE); Christian Luebbecke, Beckum (DE); Baerbel Kolbe, Witten (DE)

(73) Assignee: UHDE GmbH, Dortmund (DE)

( * ) Notice: Subject to any disclaimer, the term of this patent is extended or adjusted under 35 U.S.C. 154(b) by 461 days.

(21) Appl. No.: 12/733,204

(22) PCT Filed: Aug. 5, 2008

(86) PCT No.: PCT/EP2008/006415
§ 371 (c)(1),
(2), (4) Date: May 27, 2010

(87) PCT Pub. No.: WO2009/024259
PCT Pub. Date: Feb. 26, 2009

(65) Prior Publication Data
US 2010/0236916 A1    Sep. 23, 2010

(30) Foreign Application Priority Data
Aug. 17, 2007  (DE) .......................... 10 2007 039 074

(51) Int. Cl.
*C07C 7/00* (2006.01)
(52) U.S. Cl.
USPC ................. 585/804; 203/51; 203/57; 203/59; 585/807; 585/808; 585/833
(58) Field of Classification Search
USPC ............. 203/39–48, 51–52, 56–70; 585/804, 585/805, 807–808, 833–868
See application file for complete search history.

(56) References Cited

U.S. PATENT DOCUMENTS

| | | | |
|---|---|---|---|
| 2,439,534 | A | 4/1948 | Wilkes, Jr. |
| 2,660,581 | A | 11/1953 | Hill et al. |

(Continued)

FOREIGN PATENT DOCUMENTS

| | | |
|---|---|---|
| DE | 1 568 940 A1 | 7/1970 |
| DE | 44 37 702 C1 | 11/1995 |

(Continued)

*Primary Examiner* — Duane Smith
*Assistant Examiner* — Thomas McKenzie
(74) *Attorney, Agent, or Firm* — Marshall & Melhorn, LLC

(57) ABSTRACT

A process for the separation of the aromatic compounds benzene, toluene and xylene from an aromatics-containing reformate gasoline and pyrolysis gasoline or a coke-oven light oil or an aromatics-containing refinery stream, in which the aromatics are separated by an extractive distillation uses a novel solvent combination made up of the compounds n,n'-diformyl piperazine or 2,2'-bis-(cyanoethyl)ether in a combination with n-formyl morpholine as a second solvent for extractive distillation so that the solvent combination obtained shows a higher selectivity with regard to the aromatics to be extracted so that a lower solvent load is required. The aromatics-containing feed mixture is first submitted to a pre-distillation so that the obtained fraction has a narrow boiling point range. This fraction is then submitted to an extractive distillation in a first column, in which an aromatics-lean head product of predominantly paraffinic hydrocarbons is obtained as well as an aromatics-enriched bottom product. The bottom product is passed to a second column in which an aromatics-rich raffinate is obtained by reducing the pressure or increasing the temperature so that the extracting solvent combination obtained as bottom product can be recycled into the process.

19 Claims, 1 Drawing Sheet

(56) References Cited

U.S. PATENT DOCUMENTS

| | | | |
|---|---|---|---|
| 2,842,484 A | 7/1958 | Fleck | |
| 2,849,514 A * | 8/1958 | Nevitt | 585/856 |
| 3,434,936 A | 3/1969 | Luther et al. | |
| 3,896,007 A * | 7/1975 | Rescalli et al. | 203/33 |
| 5,107,055 A | 4/1992 | Klaumuenzner et al. | |
| 5,310,480 A | 5/1994 | Vidueira | |
| 5,433,934 A * | 7/1995 | Chang et al. | 423/235 |
| 5,723,026 A * | 3/1998 | Leisse et al. | 203/58 |
| 6,781,026 B2 | 8/2004 | Lee | |
| 2001/0049462 A1 | 12/2001 | Lee | |
| 2005/0040026 A1 * | 2/2005 | Grub et al. | 203/1 |
| 2006/0006055 A1 * | 1/2006 | Bonde | 203/73 |

FOREIGN PATENT DOCUMENTS

| | | |
|---|---|---|
| EP | 0 434 959 B1 | 1/1995 |
| EP | 0 679 708 A1 | 11/1995 |
| EP | 1 280 869 B1 | 9/2004 |
| FR | 1 376 123 A | 10/1964 |
| WO | WO 01/83642 B1 | 11/2001 |

* cited by examiner

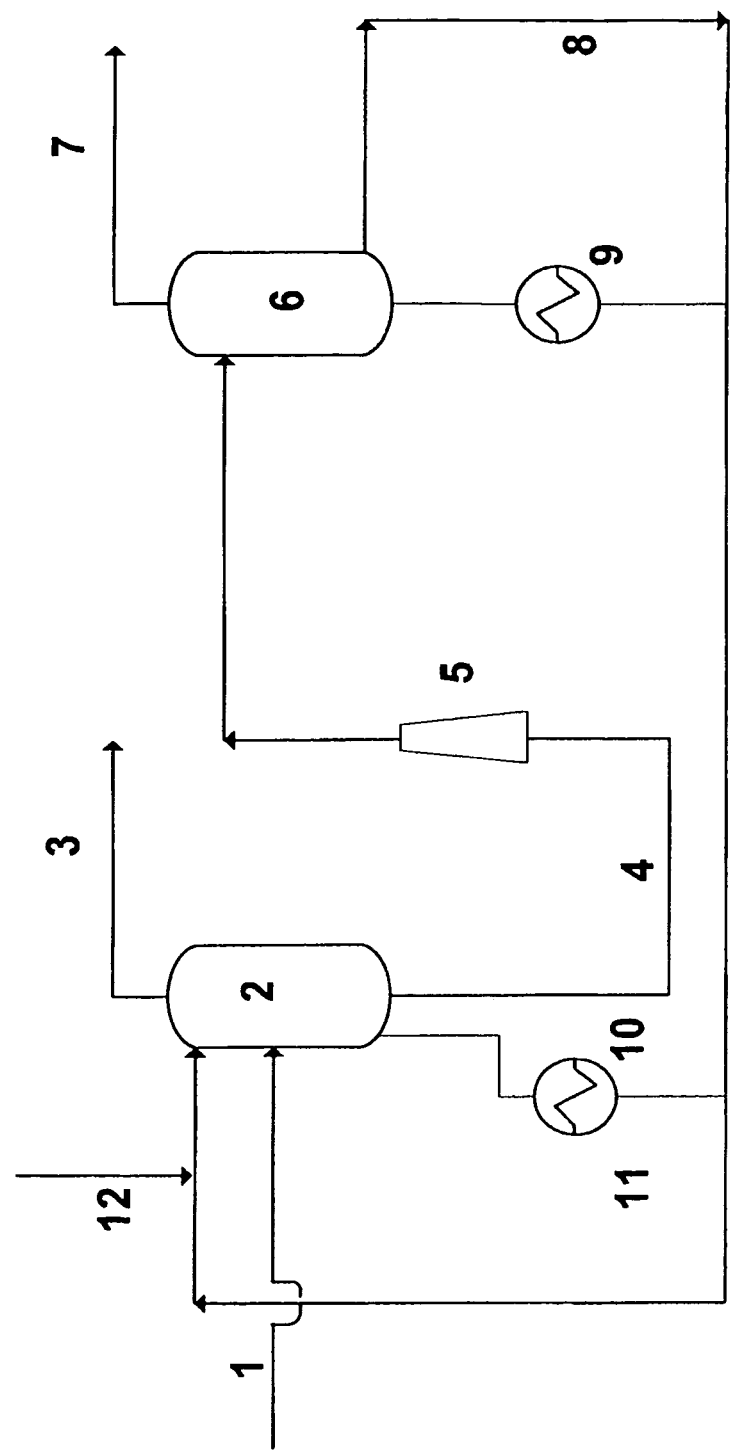

RECOVERY OF BENZENE AND BENZENE DERIVATIVES FROM GASOLINE FRACTION AND REFINERY STREAMS

BACKGROUND OF THE INVENTION

The recovery of aromatics from gasoline fractions and refinery streams is an important process step in petrochemistry and coke oven and refinery technology. Especially benzene and simple derivatives of benzene are important raw materials in the production of dyestuffs, plastics, solvents and varnishes. As these compounds in aromatics-containing fractions frequently occur in mixtures with non-aromatic compounds, process steps for their isolation are of great importance. Examples of fractions containing aromatics are reformate gasoline and pyrolysis gasoline but also distillation fractions from mineral oils or coke-oven light oil.

It is not possible to simply separate aromatics from gasoline fractions containing aromatics by way of distillation since the gasoline or its fractions consist of a large variety of substances of very similar boiling ranges. The separation is therefore to be carried out by processes which take advantage of other physical effects. The technical implementation can be achieved by several processes based on different physical separation processes. To be mentioned here in the first place are the azeotropic distillation, the liquid/liquid extraction and the extractive distillation.

In the azeotropic distillation, a solvent is added to the mixture to be separated, this solvent forming a mixture of constant boiling point with the aliphatic or the aromatic component. This azeotrope is separated from the starting mixture by distillation and after distillation fractionated into azeotrope former and aromatic fraction. In the liquid/liquid extraction, the mixture to be separated is provided with a solvent generating a two-phase mixture and involving a higher solubility of one component and thus extracting it from the solvent mixture. The aromatic component may be separated from the solvent, for example, by way of distillation after the extraction.

The extractive distillation takes advantage of the phenomenon that there is a change in the fugacities in a mixture of appropriate components. The fugacity is here to be understood as the corrected partial vapour pressure in the mixture. Reason for the change in fugacity is the fact that there are different repellent interactions between the individual types of molecules. A mixture component that has stronger repulsive forces than the other components will change into the vapour phase more easily than a component of lower repulsive forces.

In an extractive distillation a solvent is added which is known to be capable of selectively increasing the fugacity of one or several components. In the case of hydrocarbon mixtures containing aromatics, the aliphatic components of the mixture frequently have stronger repulsive forces vis-à-vis the solvent so that their fugacity is hence considerably increased. In contrast to this, the fugacity of the aromatic component changes comparatively less. For this reason, a distillation with the solvent will effect that the aliphatic components are preferably obtained in the raffinate, the low-boiling head product of a distillation, whereas the aromatic components are obtained in the extract, the higher-boiling bottom product of a distillation. This makes it necessary to use a solvent achieving the desired effect by changing the fugacities of the individual components in the desired way.

An extractive distillation frequently has advantages over an azeotropic distillation or a liquid/liquid extraction. The mass transfer in an extractive distillation frequently is considerably higher than in an azeotropic distillation as, in the case of the former, the applied temperatures are distinctly higher. An extractive distillation requires considerably less equipment than a liquid/liquid extraction, as only two distillation columns are usually required instead of one extraction column with downstream distillation unit. As considerably less solvent is required for the extractive distillation as compared to a liquid/liquid extraction, the costs of installation and operation are notably lower.

The central problem to be solved when performing an extractive distillation is the selection of a suitable solvent. From the large number of possible solvents the one is to be determined that allows the intended separation with a minimum amount of circulated solvent. Decisive criteria for this are the capacity and the selectivity of a solvent. The capacity indicates how the aromatic component in liquid state is distributed among the individual phases according to Nernst's distribution law. The higher the capacity, the better the solubility of the aromatic component in the solvent and the lower the solvent demand. The lower the capacity, the higher is the probability that a two-phase mixture is formed with the aromatic components and the solvent in liquid state. Hence the capacity mainly determines how much solvent is required.

The selectivity indicates the improvement of the extraction of the desired transition component in comparison to the other components contained in the raffinate. The higher the selectivity of an extracting agent, the stronger is the repulsion of the aliphatic component and thus the corresponding change in fugacity. The selectivity essentially determines the separating efficiency and thus the number of theoretical trays required for the extractive distillation. The lower the selectivity, the more equipment is required.

Various solvents suited for an extractive distillation of aromatics are known. Frequently used solvents are diethylene glycol, dimethylsulfoxide, sulfolane, n-methylpyrrolidone, dimethylacetamide and n-formyl morpholine. A hydrocarbon stream is used as a feed mixture, which contains aromatic and aliphatic components and is distilled in a pre-distillation unit to give a hydrocarbon with a relatively narrow boiling point range. Depending on the separating efficiency of the extractive distillation, the feed stream is a $C_6$-stream, a $(C_6\text{-}C_7)$-stream or a $(C_6\text{-}C_8)$-stream.

The actual equipment for the extractive distillation usually consists of two distillation columns. The first column serves to perform the actual extractive distillation. At the head of the column a raffinate stream is obtained which predominantly consists of non-aromatic hydrocarbons and, depending on the configuration, a certain amount of solvent. As the repulsive effect of the solvent is stronger for the non-aromatic hydrocarbons, these compounds change to the vapour phase more easily. At the lower part of the column a mixture is obtained which predominantly consists of aromatic compounds and the extracting solvent. This mixture is then passed into a stripping column where the aromatics-containing mixture is separated from the solvent by way of distillation. The solvent is recycled back to the first column.

The distillative separation of the extract gives a hydrocarbon mixture rich in aromatics as a fraction at the head of the stripping column and a solvent fraction as bottom product which is lean in aromatics. Both fractions may be passed to a downstream purification. Once purified, the aromatics may, for instance, be further processed by distillation to obtain the individual aromatic compounds by alkylation degree and boiling point. Thus the benzene derivatives benzene, toluene and xylene are obtained. To separate the xylene isomers, further process steps may follow. As a purification step for the aromatics fraction, a scrubbing process with water may be advisable.

DE 1568940 C3 describes a process for the extractive distillation of aromatics using n-formyl morpholine as a solvent. The process can be used for the isolation of aromatics from a starting fraction containing aromatics as well as for the removal of aromatics from hydrocarbon streams. This process is run in a facility including a column for extractive distillation, a solvent stripper, a stripping column and a solvent regeneration column. Depending on purity and requirements, the aromatics contained can be obtained either directly or be submitted to further treatment. Owing to the relatively low solvent capacity this process requires a high amount of solvent and involves high constructional cost.

EP 679708 A1 describes an extraction process which requires only one extraction column owing to a specific equipment arrangement. The extraction is carried out in a column from which a head product rich in aliphatic compounds is obtained and a side product which is rich in aromatics from the middle column section. The solvent is recycled from the bottom via heat-exchanging devices to the upper column section. Both hydrocarbon streams are freed from excessive solvent and water in cyclone separators and downstream phase separators. As solvents, preferably polyalkylene glycols are used but also sulfolanes or pyrrolidones. To improve the separating efficiency, 0.1 to 20 mass percent of water are added to the solvent mixture. A disadvantage of this process is that the separating efficiency can only be improved if a certain amount of water is added. This makes it necessary to install additional devices for drying the products obtained.

EP 1280869 B1 describes a process for the extractive distillation of a hydrocarbon mixture containing aromatics using a solvent mixture of sulfolane and 3-methyl sulfolane. The solvent mixture can be used in any ratio desired and thus adapted to the aromatics content and the composition of the aromatics portion to an optimum degree. This process is run in a facility consisting of a column for extractive distillation and a column for distillation of the aromatic fraction. By such arrangement the process can be run with a relatively low demand for equipment. The disadvantage of this process is a large amount of circulated solvent and a relatively large column for extractive distillation, as a large portion of extracting solvent combination as compared to the hydrocarbon must be used.

BRIEF SUMMARY OF THE INVENTION

The aim of the invention is to find a solvent and a suitable process for the extractive distillation of benzene derivatives from gasoline fractions, which is characterised by improved properties as regards the aspects of selectivity and capacity. The capacity of the solvent should be adequately high so that a relatively little amount of circulated solvent is required. The solvent cost should be low and the demand for equipment low. The achieved selectivity of the solvent should be high so to ensure adequate shifting of the boiling point of the aliphatic component and easy isolation of the paraffinic and aromatic hydrocarbons from the gasoline fraction.

The present invention achieves the aim by using a new solvent mixture which meets the specified requirements. It was found that the two solvent additives n,n'-bis-(formyl) piperazine or 2,2'-bis-(cyanoethyl)ether in combination with n-formyl morpholine are especially well-suited for the extractive distillation of aromatics. The capacity of this solvent combination is so high that the aromatics can be separated from the gasoline fraction with an only small amount of extracting agent. The selectivity in relation to aromatics is so high that, after addition of the extracting solvent, the boiling points of the aromatic compounds differ sufficiently enough for a distillative separation. By the high selectivity of the solvent combination according to the invention, the non-aromatic hydrocarbons are almost completely separated from the gasoline fraction so that, after the removal of the extracting solvent, it will be possible to carry out a simple distillation separation of the aromatics benzene, toluene and of the xylenes.

By the variable selectivity-increasing effect of the additional solvent components according to the invention, it is possible to reduce the amount of circulated solvent mixture to an extent that the capacity limit or, in other words, the phase separation of solvent and aromatics mixture is almost reached. The solvent combination can be optimised such that it will bring a maximum saving of solvent load for every gasoline fraction. A lower amount of circulated solvent involves lower investment cost and utility cost with plant capacity and product purity remaining the same.

DETAILED DESCRIPTION OF THE INVENTION

Claimed is a process for the recovery of a pure aromatics fraction containing benzene, toluene or xylene or mixtures of these aromatics from refinery streams or gasoline fractions containing such aromatics by way of extractive distillation, in which
the feed product is subjected to a pre-distillation in a first process step prior to the extractive distillation, where the components which boil at higher temperatures than the mentioned aromatics are separated as a bottom product, and
the thus obtained starting mixture containing aromatics is mixed in a second process step with an extracting solvent or solvent mixture which is capable of selectively increasing the fugacity of the non-aromatic components of the starting mixture and thus the separating efficiency, and submitted to an extractive distillation, and
the extracting solvent from the obtained extract is distilled off in a third process step by increasing the temperature or increasing the temperature and reducing the pressure,
characterised in that
the extractive distillation of the second process step is carried out using a solvent combination comprising n,n'-diformyl piperazine with another solvent or 2,2'-bis-(cyanoethyl)ether with another solvent as vapour-pressure changing solvent combination.

The solvents according to the invention may be used either in a mixture or as individually as solvent components. In a preferred embodiment they are used in a mixture with a solvent which is not in accordance with the invention. A preferred solvent combination is n-formyl morpholine in a mixture with one of the two solvent components according to the present invention.

By the novel solvent combination it is possible to save a notable amount of circulated solvent. If a solvent combination of the solvents n,n'-diformyl piperazine and n-formyl morpholine in a mass ratio of 1:1 is admixed, 10 to 30 mass percent of circulated solvent can be saved as compared to the pure solvent n-formyl morpholine. In a preferred embodiment of the invention, the saving in the amount of circulated solvent ranges between 15 and 25 mass percent.

If a solvent combination of the solvents 2,2'-bis-(cyanoethyl)ether and n-formyl morpholine in a mass ratio of 1:1 is admixed, 5 to 15 mass percent of circulated solvent can be saved as compared to the pure solvent n-formyl morpholine. In a preferred embodiment of the invention, the saving as compared to the solvent n-formyl morpholine ranges between 7 and 11 mass percent.

N,n'-diformyl piperazine or hexahydro-1,4-diazine-1,4-dimethanal (HCO[cyclo-N(CH$_2$CH$_2$)$_2$N]CHO) is a chemical substance which is easy to procure and frequently used for the recovery of fine chemicals. 3,3'-oxydipropionitril or 2,2'-bis-(cyanoethyl)ether (NC(C$_2$H$_4$)O(C$_2$H$_4$)CN) is a chemical substance which is easy to procure and frequently used as a solvent in chromatography owing to its specific polar characteristics. This chemical can be produced easily so that larger amounts of the compounds are available at reasonable price. The melting point of the compound n,n'-diformyl piperazine which is solid at room temperature is at 125 to 129° C., melting and boiling point of the compound 2,2'-bis-(cyanoethyl)ether which is liquid at room temperature is at −26° C. and 130 to 132° C. (0.26 kPa).

To run the process according to the invention the two solvents according to the invention are preferably used in combination with a second solvent in order to keep the boiling point of the extracting solvent combination within a range suitable for the separation of the solvent. If the boiling point is too high, it is possible that the extracting solvent decomposes when the solvent is separated from the aromatics. The addition of a solvent not in accordance with the invention lowers the boiling point of the solvent combination according to the invention so that a decomposition of solvent components can be avoided without being forced to keep the pressure at a low level.

In another embodiment of the invention, substituted heterocyclic compounds containing nitrogen and oxygen are added as a second solvent. Especially suitable as a second solvent is n-formyl morpholine. The second solvent can be added to the solvent according to the invention in greatly varying weight percentages to achieve the effect according to the invention. Preferred for running the process according to the invention is a ratio of the two solvents of 1:1.

In a further embodiment of the invention, the solvent components according to the invention are used in the form of derivatives. Thus it is possible, for example, to introduce carbonaceous substituents into the solvent component according to the invention without any essential changes of the characteristics responsible for the extraction. To keep the solubility of the extracting solvent in a range suitable for the process according to the invention, the number of the C atoms of all substituents is not larger than 7.

Claimed in addition to the described process for extractive distillation is a substance mixture which consists in the compounds n,n'-diformyl piperazine and n-formyl morpholine. Also claimed is a substance mixture which consists in the compounds n,n'-diformyl piperazine and 2,2'-bis-(cyanoethyl)ether. The mixtures have not yet been provided or described as a substance in this form. Claimed as well is the use of the substance mixtures according to the invention for the extractive distillation.

The process according to the invention is run by means of an apparatus typical of the extractive distillation of aromatics. An exemplary apparatus is described in EP 434959 A2. The aromatics-containing feed mixture obtained from the pre-distillation of the gasoline is pre-heated and fed into the bottom part of a first distillation column provided for extraction. The latter has already been loaded with the extracting solvent combination according to the invention. In the extractive distillation, a raffinate stream is obtained at the head of the column, which contains a considerably depleted amount of aromatic hydrocarbons and essentially contains paraffinic hydrocarbons or perhaps a certain amount of naphthenic hydrocarbons. This raffinate stream contains a very little amount of extracting solvent only and, as soon as obtained, can, if required, be transferred to a downstream treatment such as, for example, a scrubbing unit. As a bottom product of the extraction column, an extract stream strongly enriched with aromatic hydrocarbons in a mixture with the extracting solvent. In an embodiment of the invention, the extractive distillation is carried out at reduced pressure.

The extract stream is fed into the bottom part of the second distillation column which is also referred to as the stripping column. The latter is provided for the distillative separation of the solvent from the aromatics to be obtained. As a bottom product of this column, the solvent is recovered and recycled via a line into the upper part of the first column which is provided for the extractive distillation. In this way it is possible to establish an essentially closed loop for the extracting solvent combination. To heat the two columns, they may optionally be equipped with a reboiler circuit.

As a head product of the second column provided for solvent separation, a hydrocarbon stream essentially free of solvent is obtained, which primarily contains the desired aromatic hydrocarbons. As soon as obtained, this aromatic stream can be transferred to a downstream treatment unit.

In an embodiment of the invention, the aromatic stream obtained from the solvent separation is transferred to an optional scrubbing process with water to remove any remainders of the solvent combination obtained. The scrubbing process may be followed by further processing steps in phase separators. Upon receipt, the solvent-free extract produced is preferably submitted to a distillative separation, in which the individual benzene derivatives are obtained in an amount which corresponds to the portion of the individual aromatics in the starting mixture. A specific advantage of the process according to the invention is that it is possible in this distillation to obtain the xylenes, which are harder to obtain, as a pure xylene fraction.

In a further embodiment of the invention the separation of the extracting solvent from the aromatics is performed at reduced pressure. In this way it is possible to limit the thermal load of the extracting solvent combination and to reduce the equipment required for cooling the extract stream. To allow that the solvent be separated in the second distillation column at reduced pressure, the gas pressure of the raffinate stream obtained from the first column provided for the extraction is decreased by a suitable device.

The effect according to the invention could be supported by theoretical VLE (vapour liquid equilibrium) data-based calculations. The process according to the invention was simulated in a process which was calculated by entering the main plant parameters into the Aspen Plus computer program of Aspen Tech make. Input data were temperature, pressure, boiling point, interaction parameters and solubility of all specified compounds. Used in the simulated process was a distillation unit which was typical of an extraction process for single aromatic hydrocarbons. To demonstrate the effect according to the invention, the pure solvent n-formyl morpholine was compared with the solvent combinations according to the invention, i.e. n,n'-diformyl piperazine with n-formyl morpholine and 2,2'-bis-(cyanoethyl)ether with n-formyl morpholine. Both solvent combinations were specified with a mass ratio of 1:1 in the simulation calculation. The solvent amounts which were obtained as a result at important process points were converted into percent by weight for the calculated saving in the amount of circulated solvent. The fault tolerance of this computer program amounted to ±10% for the percent figures of solvent saving.

To achieve an advantageous energetic balance of the process, the hot bottom product obtained from the solvent separation, which essentially consists of extracting solvent, can be recycled to the process via heat-exchanging devices. The hot bottom product from the stripping column may be used for heating the feed mixture, for heating the first column provided for extractive distillation or for heating the second column provided for solvent separation.

In the event of continuous operation of the plant for the recovery of aromatics, a slight loss in extracting solvent may occur despite all the measures taken. Solvent may get into the downstream treatment processes via the raffinate streams from the low-boiling fractions. To compensate such loss, pre-heated fresh solvent may be fed to the process by suitable devices at the head of the first column.

The fed amount is controlled such that the weight ratio of used solvent to hydrocarbon mixture used ranges between 1:1 and 5:1. In a preferred embodiment of the invention the weight ratio of the used solvent combination and the used hydrocarbon mixture ranges between 2:1 and 3:1, provided the solvent components according to the invention are used in a mixture with n-formyl morpholine.

In an embodiment of the invention, the distillation temperature in the first column provided for extraction is adjusted such that the raffinate discharged at the head of the column is of a temperature of at least 50° C. at atmospheric pressure and the bottom product obtained at the lower end of the column is of a maximum temperature of 200° C. The boiling temperatures inside the column may change if the distillation pressure or the composition of the hydrocarbon mixture changes.

In another embodiment of the invention, the temperature in the second column provided for solvent separation is adjusted such that the raffinate discharged at the head of the column is of a temperature of at least 50° C. and the maximum temperature of the bottom product at the lower end of the column is 260° C. Here, the maximum temperature is essentially determined by the decomposition temperature of the solvent. The boiling temperatures inside the column may change if the distillation pressure or the composition of the hydrocarbon mixture changes.

In a further embodiment the solvent is provided with a low water portion to increase the selectivity of the extractive distillation. The water content may range between 0.1 and 20 mass percent, preferably, however, between 0.5 and 10 mass percent. This depends on the process and equipment conditions selected for the respective device.

The process according to the invention can be used for isolating aromatics from an aromatics-containing starting fraction as well as for purifying hydrocarbon streams from aromatics. The removal of aromatic compounds from a mainly paraffinic mixture may be of interest to the foodstuff industry, for example. As starting gasoline fractions, hydrocarbon streams from mineral oil processing and from refineries may be used as well as products obtained from coke oven or hydrocarbon producing plants as, for instance, coke-oven light oil.

Running the process according to the invention does not require any essential changes in equipment as compared to conventional extractive distillation processes. The capacity of the solvent used rises significantly so that altogether less solvent is required for circulation in the overall loop. The solvent components used according to the invention reduce the amount of circulated solvent and thus reduce the cost as well. The lower amount of circulated solvent brings about lower investment cost while plant capacity and product purity remain the same. The selectivity of the solvent mixture also increases significantly so that it is possible to adapt the solvent optimally to the aromatics content and the aromatics distribution in the feed mixture.

The configuration of the process according to the invention for the recovery of benzene derivatives from gasoline fractions and refinery streams is illustrated in more detail by means of an example and a drawing, the process according to the invention not being restricted to this embodiment.

EXAMPLE

The attached table (Table 1) outlines the saving of solvent in the process according to the invention using the solvent combination according to the invention as compared to the conventional n-formyl morpholine.

TABLE 1

| Solvent combination (mass ratio) | Saving of solvent as compared to n-formyl morpholine |
|---|---|
| N,n'-diformyl piperazine + n-formyl morpholine (1:1) | 10 to 30 mass percent |
| 2,2'-bis-(cyanoethyl)-ether + n-formyl morpholine (1:1) | 5 to 15 mass percent |

The attached drawing (FIG. 1) shows an exemplary embodiment of the process for extracting aromatics from a gasoline fraction.

Via a feed line 1, an aromatics-containing feed mixture obtained from a pre-distillation unit is fed to the middle section of a column 2 which is provided for the extractive distillation of the aromatics-containing mixture. The column has already been loaded with the solvent according to the invention in combination with another solvent. The distillation produces a raffinate which is an aromatics-lean hydrocarbon stream 3 mainly containing paraffinic hydrocarbons and being passed to further processing. The bottom product obtained is an aromatics-enriched hydrocarbon stream 4 which is passed via a line with pressure-reducing device 5 to a second column 6 for solvent separation. In this column the solvent is separated by increasing the temperature and/or reducing the pressure. As a head product, an aromatics-rich extract 7 is obtained which is largely free of solvent. As a bottom product, a solvent stream is obtained which mainly contains the aromatics-lean solvent. This is returned via a line 8 into the upper part of column 2 provided for extractive distillation. Via indirect heat exchange by means of heat-exchanging devices 9, 10 and 11, the solvent can be used to heat starting mixture 1, extraction column 2 or stripping column 6. By adding solvent or solvent components via a separate feed nozzle 12 it is possible to compensate the loss in solvent during continuous operation.

| List of reference numbers and designations | |
|---|---|
| 1 | Starting mixture feed line |
| 2 | Extractive distillation column |
| 3 | Raffinate, product stream of aromatics-lean hydrocarbon mixture |
| 4 | Line for aromatics-rich solvent mixture |
| 5 | Pressure-reducing device |
| 6 | Stripping column for the separation of solvent |
| 7 | Product stream of aromatics-rich hydrocarbon mixture |
| 8 | Solvent recycle line |
| 9 | Heat exchanger |
| 10 | Heat exchanger |
| 11 | Heat exchanger |
| 12 | Solvent feed nozzle |

The invention claimed is:

1. A process for the recovery of a pure aromatics fraction containing benzene, toluene or xylene or mixtures of these aromatics from refinery streams or gasoline fractions as feed products containing such aromatics by way of extractive distillation, comprising:
subjecting the feed product to a pre-distillation in a first process step prior to the extractive distillation, where the components which boil at higher temperatures than the mentioned aromatics are separated as a bottom product, and
mixing the thus obtained starting mixture containing aromatics in a second process step with an extracting solvent or solvent mixture which is capable of selectively increasing the fugacity of the non-aromatic components of the starting mixture and thus the separating efficiency, and submitted to an extractive distillation, and
distilling the extracting solvent from the obtained extract off in a third process step for the separation of the extracting solvent by increasing the temperature or increasing the temperature and reducing the pressure,
wherein the extractive distillation of the second process step is carried out using a solvent combination comprising N,N'-diformyl piperazine with another solvent or using a solvent combination of 2,2'-bis-(cyanoethyl)ether with N,N'-diformyl piperazine or N-formyl morpholine as a vapour-pressure changing solvent combination.

2. The process according to claim 1, wherein the extractive distillation is carried out with a solvent comprising a substituted derivative of the N,N'-diformyl piperazine compound, in which the C-number of the substituents is not larger than 7 C-atoms.

3. The process according to claim 1, wherein the extractive distillation is carried out with a solvent comprising a substituted derivative of the 2,2'-bis-(cyanoethyl)ether compound, in which the C-number of the substituents is not larger than 7 C-atoms.

4. The process according to claim 1, wherein the extractive distillation is carried out with a solvent mixture of N,N'-diformyl piperazine and N-formyl morpholine.

5. The process according to claim 1, wherein the extractive distillation is carried out at a mass ratio of feed mixture to solvent in a range between 1:1 and 1:10.

6. The process according to claim 1, wherein the used solvent or the used solvent combination contains a water portion of 0.1 to 20 mass percent.

7. The process according to claim 1, wherein the aromatics-rich mixture obtained from the extractive distillation is submitted to a scrubbing process with water after separation of the solvent.

8. The process according to claim 1, wherein an aromatic fraction containing benzene, toluene and xylene as a mixture of these aromatics from refinery streams or gasoline fractions is used as a feed product, and the aromatics-rich mixture obtained from the extractive distillation is further fractionated into a first fraction containing benzene, a second fraction containing toluene and a third fraction containing xylene after separation of the solvent.

9. The process according to claim 1, wherein the extractive distillation is carried out in a first distillation column from which an aromatics-lean hydrocarbon stream is obtained as low-boiling raffinate.

10. The process according to claim 1, wherein the solvent separation is carried out in a second distillation column from which an aromatics-rich hydrocarbon stream is obtained as low-boiling raffinate.

11. The process according to claim 1, wherein the solvent for the extractive distillation is circulated in a closed loop.

12. The process according to claim 1, wherein the extracting solvent from the solvent separation can be recycled as high-boiling bottom product from the second column for the solvent separation into the head of the first column for the extractive distillation.

13. The process according to claim 1, wherein the loss in solvent can be compensated by feeding extracting solvent or an extracting solvent mixture.

14. The process according to claim 1, wherein the extractive distillation in the first column is carried out at a temperature of 200° C. at the bottom of this column and a temperature of 50° C. at the head of this column.

15. The process according to claim 1, wherein the solvent separation in the second column for the solvent separation is carried out at a temperature of 260° C. at the bottom of this column and a temperature of 50° C. at the head of this column.

16. The process according to claim 15, wherein the solvent separation in the second distillation column is carried out at reduced pressure.

17. The process according to claim 1, wherein the solvent stream from the solvent separation is used for heating the feed mixture provided for the extractive distillation via heat-exchanging devices.

18. The process according to claim 1, wherein the solvent stream from the solvent separation is used for heating the first distillation column provided for extractive distillation via heat-exchanging devices.

19. The process according to claim 1, wherein the solvent stream from the solvent separation is used for heating the second distillation column provided for solvent separation via heat-exchanging devices.

* * * * *

UNITED STATES PATENT AND TRADEMARK OFFICE
CERTIFICATE OF CORRECTION

PATENT NO.       : 8,536,397 B2  
APPLICATION NO. : 12/733204  
DATED            : September 17, 2013  
INVENTOR(S)      : Noll et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this

Fifteenth Day of September, 2015

Michelle K. Lee
*Director of the United States Patent and Trademark Office*